(12) United States Patent
Pickenhagen et al.

(10) Patent No.: US 6,734,159 B2
(45) Date of Patent: May 11, 2004

(54) ISOLONGIFOLENYL ETHERS, THEIR PREPARATION AND THEIR USE

(75) Inventors: Wilhelm Pickenhagen, Höxter (DE); Dietmar Schatkowski, Stadtoldendorf (DE)

(73) Assignee: Symrise GmbH & Co. KG (DE)

( * ) Notice: Subject to any disclaimer, the term of this patent is extended or adjusted under 35 U.S.C. 154(b) by 0 days.

(21) Appl. No.: 10/396,608

(22) Filed: Mar. 25, 2003

(65) Prior Publication Data

US 2003/0166974 A1 Sep. 4, 2003

Related U.S. Application Data

(62) Division of application No. 09/920,693, filed on Aug. 2, 2001.

(30) Foreign Application Priority Data

Aug. 3, 2000 (DE) .......................... 100 38 544

(51) Int. Cl.$^7$ ................................. A61K 7/46
(52) U.S. Cl. .............. 512/19; 512/9; 512/23; 512/25; 510/104; 510/506; 568/665; 568/667
(58) Field of Search .............. 512/9, 19, 23, 512/25; 510/104, 506; 568/665, 667

(56) References Cited

U.S. PATENT DOCUMENTS 3,647,847 A * 3/1972 Curtis et al. ............. 560/249
3,718,698 A * 2/1973 Hall ........................ 568/342
4,100,110 A * 7/1978 Ansari et al. ............. 512/18
4,782,192 A * 11/1988 Light et al. ............... 568/665
5,693,606 A * 12/1997 Brunke et al. ............. 512/19

* cited by examiner

*Primary Examiner*—Rosalynd Keys
(74) *Attorney, Agent, or Firm*—Pendorf & Cutliff

(57) ABSTRACT

Cyclic isolongifolenyl ethers of the general formula A, where wavy lines mean α- and β-configuration, and R is the following radicals.

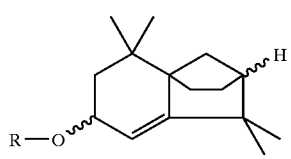

A

Figure 1:
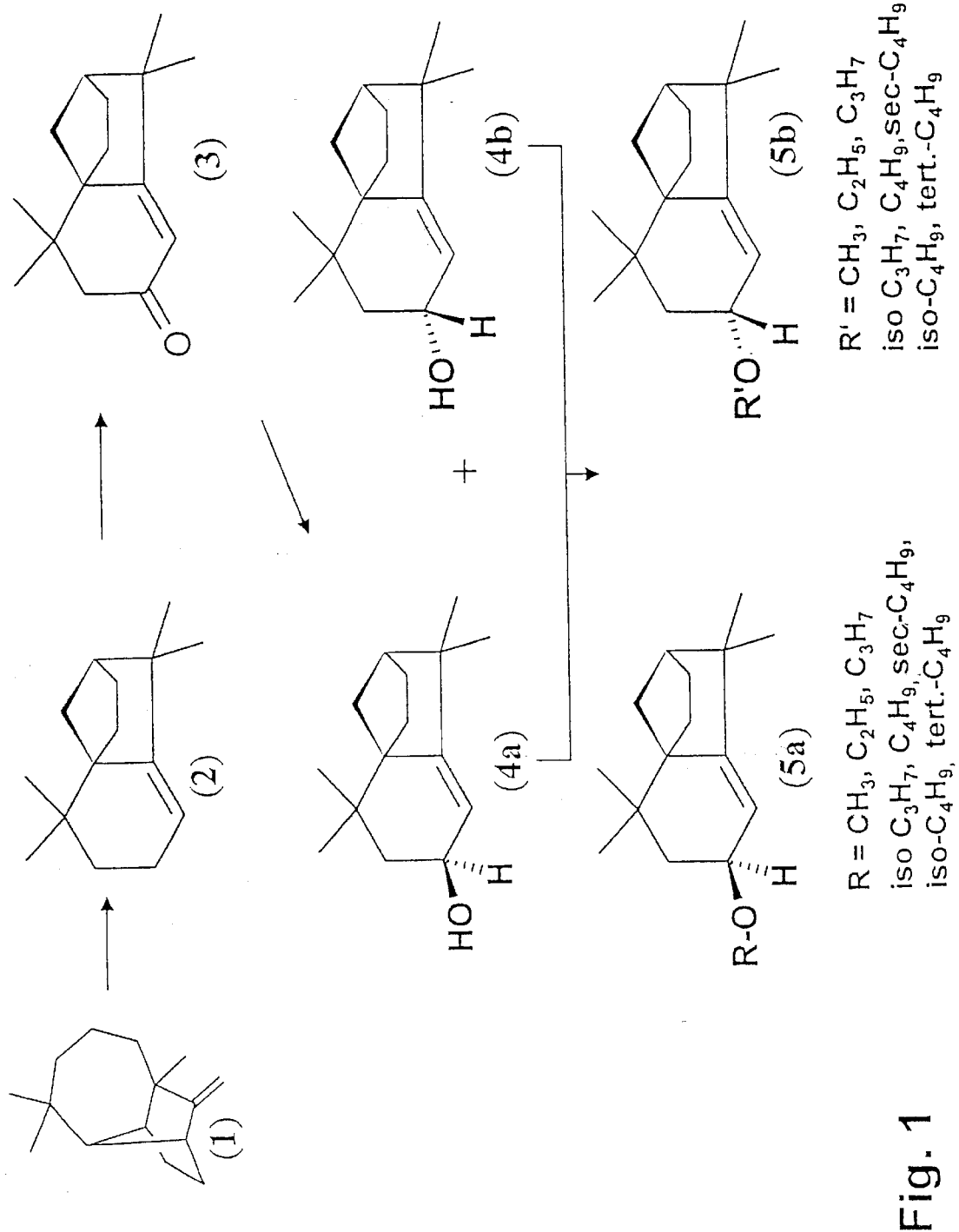

R=Me, Et, Pr, iso-Pr, Bu, sec-Bu, iso-Bu, tert-Bu. These isolongifolenyl ethers are excellent fragrances and can, in particular, be used as a constituent of fragrance mixtures or perfume oil for the perfuming of cosmetic or technical consumer goods. Also described are processes for the preparation of said cyclic isolongifolenyl ethers.

13 Claims, 1 Drawing Sheet

ISOLONGIFOLENYL ETHERS, THEIR PREPARATION AND THEIR USE

This application is a divisional of application Ser. No. 09/920,693 filed Aug. 2, 2001.

BACKGROUND OF THE INVENTION

1. Field of the Invention

Industrially prepared perfume oils nowadays consist for the greatest part of synthetic fragrances.

2. Description of the Related Art

Although the traditional use of essential oils and extracts of a vegetable and animal origin continues to play an important role in the field of alcoholic (fine) perfumery, the perfuming of laundry detergents, soaps, household cleaners and similar technical products requires the use of fragrances which satisfy the technical requirements with regard to stability and substantivity. In order to correspond with these particular requirements, perfumes for use in technical consumer goods are largely formulated from synthetic fragrances. However, because these perfumes are needed in large amounts, all of the important perfume houses and fragrance manufacturers of aroma substances have in the last few decades directed their research activities to the preparation of novel synthetic fragrances.

In the meantime, synthetically prepared fragrances which in the past have been prepared essentially for technical use because of their comparatively low price and their high stability, have increasingly been used in fine perfumery as well.

Meanwhile there is a constant need for fragrances with improved properties, such as odor quality, stability, skin compatibility and environmental compatibility. For the purposes of a good ecobalance, products are strived for here which are based on renewable raw materials.

One raw material of natural origin which is available in relatively large amounts is the sesquiterpene longifolene (1), which occurs as the main component in Indian turpentine oil and as a secondary component in numerous other types of turpentine oil and other essential oils. Even more than 2 decades ago a number of secondary products from longifolene had been prepared and the fragrance properties thereof described. G. Ohloff reports in his book "Riechstoffe und Geruchssinn" [Fragrances and Sense of Smell] [Springer-Verlag, 1990, ISBN No. 3-540-52560-2, pages 87–88] in summary that at least 4 commercial fragrances are derived from (+)-longifolene (1), and 13 fragrance derivatives can be commercially utilized from the isolongifolene (2) accessible therefrom by isomerization. Some of these derivatives are given the characteristic odor type woody (odor of wood) by Ohloff; other odor notes are not mentioned.

The chemistry and odor properties of the commercially important derivatives of isolongifolene (2) have been reported by G. Färber and H. Tan [G. Färber, Parfümerie+Kosmetik, 68, 18 (1987), H. Tan, Parfümerie+Kosmetik, 67, 564 (1986)]. In this connection, the last-named publication in particular reveals that the isolongifolene derivatives known as fragrance can be used instead of the known wood scent note because of their woody character.

Our publication EP-A 0 543 470 describes cyclic isolongifolanone ketals of the general formula B

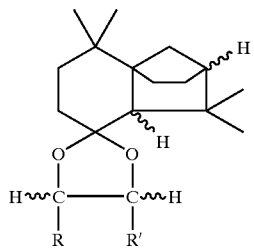

(in which wavy lines are α- and β-configuration, and R and R' are hydrogen or methyl or ethyl radicals). These ketals are valuable fragrances which have strong woody odor properties with floral-fresh effects and velvety moss/ambergris character.

Our publication EP-A 0 669 308 describes isolongifolanole derivatives of the general formula C

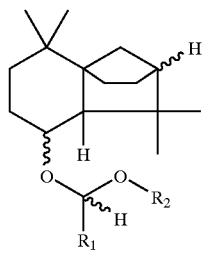

(in which wavy lines are α- and β-configuration, and R1 is hydrogen or methyl radicals and R2 is methyl or ethyl radicals). These derivatives likewise have woody olfactory properties.

GB-A 1 505 821 describes isolongifolanole and lower esters thereof (acyl groups with up to 6 carbon atoms) as fragrances, the α-/β-isometry of the hydroxyl or carboxyl function being discussed. Said fragrances have strong woody odor properties reminiscent of cedryl acetate and vetiveryl acetate and are particularly highly suitable for perfume compositions with floral or citrus-woody character.

GB-A 1 256 535 describes the controlled oxidation of isolongifolene (2) to isolongifolenone (3) and subsequent reduction thereof to isolongifolenol (4). The subsequent esterification (acyl groups having up to 5 carbon atoms) of the virtually odorless isolongifolenol (4) again leads to fragrances (isolongifolenyl esters) with a woody odor profile.

According to the prior art just given, the field of longifolene and isolongifolene derivatives appears to have been investigated particularly thoroughly. In addition to a limited number of longifolene and isolongifolene derivatives with valuable fragrance properties (cf. in particular the abovementioned prior art), there is an utterly confusingly large number of derivatives of the abovementioned sesquiterpenes described in the literature or synthesized and investigated by ourselves which are of little or no significant olfactory value.

Even if some of the known isolongifolene derivatives have excellent olfactory properties and can be prepared on an industrial scale in a manner which is both low in cost and also environmentally compatible, it would nevertheless, looking at the group of isolongifolene derivatives as a whole, increasingly be perceived as disadvantageous and restrictive that for isolongifolenol derivatives with a noteworthy olfactory activity, a woody aspect frequently is in the foreground, which limits the use spectrum of the derivatives.

SUMMARY OF THE INVENTION

It was therefore the primary object of the present invention to provide a fragrance, preferably an isolongifolene derivative or a group of isolongifolene derivatives, and a process for the preparation thereof, where, compared with the isolongifolene derivatives of olfactory interest mentioned before, at least not only the woody, but also other odor aspects should be in the foreground. Advantageously, the nonwoody aspects should be dominant here.

In connection with this, a further object was to provide a perfume composition whose olfactory properties are codetermined by a fragrance, preferably an isolongifolene derivative or a mixture of isolongifolene derivatives, for which at least not only woody but also other odor aspects are in the foreground.

Further objects on which the present invention is based can be formulated as follows: The isolongifolene derivative or the mixture of isolongifolene derivatives should as far as possible be able to contribute to a long-lasting after-odor and to a good fixing of a perfume composition.

The isolongifolene derivative or the mixture of isolongifolene derivatives should as far as possible be able to contribute in a perfume composition to a rounding off and harmonizing of the main note (the "bouquet").

Finally, a further object of the present invention was to provide a process with which a material (a substance) can have added to it a (not primarily woody) odor or have its (intrinsic) odor intensified, by adding an isolongifolene derivative or a mixture of isolongifolene derivatives to the material (the substance).

Finally, a further object of the present invention was to provide a process with which a material (a substance) can have added to it a (not primarily woody) odor or have its (intrinsic) odor intensified, by adding an isolongifolene derivative or a mixture of isolongifolene derivatives to the material (the substance).

There is particularly great interest in this connection in fragrances with a musk character. The isolongifolene derivatives used hitherto as fragrances do not usually have a musk character of this type. To prepare perfume oils with a musk note, it is therefore necessary to mix one of the known musk fragrances with the respective isolongifolene derivative.

Thus, for example, the already mentioned GB-A 1 256 535, inter alia, recommends mixing the isolongifolenol esters described therein with a musk compound, such as musk ketone or ethylene brassylate.

In the likewise already mentioned GB-A 1 505 821, musk compounds are likewise among the preferred compounds for mixing with the disclosed isolongifolene derivatives.

The situation is similar also with regard to the compounds disclosed in our own specified publications.

DETAILED DESCRIPTION OF THE INVENTION

According to the invention, the proposed object is achieved by the provision and use of the novel compound of the general formula A

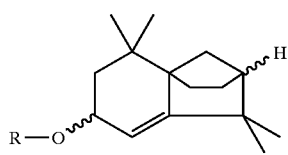

(in which wavy lines are α- and β-configuration, and R=methyl, ethyl, propyl, iso-propyl, butyl, sec-butyl-, iso-butyl, tert-butyl radicals).

The individual compounds covered by this general formula, and mixtures thereof (i.e. enantiomer mixtures and/or mixtures of pure or mixed enantiomers having different radicals R) have quite unique odor properties and also differ markedly from the known fragrances from the family of isolongifolenol derivatives discussed above. For example, the novel individual compounds covered by general formula A interestingly have only very weak woody odor properties. Instead, they are characterized by a strong, smooth, velvety musk/ambergris odor; in some cases, a patchouli aspect can also be established in the after-odor. The above odor characteristics apply in particular to (individual) compounds of the general formula A where R=methyl, ethyl, propyl, and iso-propyl (in each case pure enantiomer or enantiomer mixture). For mixtures of said individual compounds with a different alkyl radical in the ether function, corresponding statements apply.

Furthermore, in perfume compositions with a floral accent, the individual compounds covered by general formula A, and mixtures thereof, intensify in a synergistic manner the floral effect and refresh this effect, in particular in the top note.

The individual compounds (pure enantiomers or enantiomer mixtures) according to the invention covered by the general formula A are particularly long-lasting and fixing.

Cyclic isolongifolenyl ethers of the general formula A where R=Me, Et, Pr or iso-Pr, in which the configuration of the ether function is α or β or the cyclic isolongifolenyl ether comprises a mixture of enantiomers which differ in the configuration of the ether function are, however, preferred in this respect over the ethers (pure enantiomer or enantiomer mixture) of the general formula A where R=butyl, sec-butyl, iso-butyl or tert-butyl.

Of these, particular preference is in turn given to the isomer ethers of the general formula A where R=methyl (pure enantiomer or enantiomer mixture) because of (a) their particular odor characteristics (with musk aspects) which influence in particular the after-odor of a perfume composition,
(b) their high fixing ability and their good adhesion to customary substrates,
(c) their ability to be used for intensifying in particular floral top notes and
(d) their ability to be used for rounding off and harmonizing certain main notes for use in perfumery.

The isomeric ethers of the general formula A where R=ethyl, propyl or iso-propyl (pure enantiomer or enantiomer mixture) likewise have surprisingly marked odor characteristics which influence the after-odor of a perfume composition, but are overall not quite so odor-intensive as the isomers of the general formula A where R=methyl. They are therefore intended in particular for the rounding off and harmonizing of certain main notes.

To prepare the methyl ethers covered by the general formula A, (+)-longifolene (1) was, isomerized according to the process diagram in FIG. 1 in a known manner by treatment with a mixture of acetic acid and sulfuric acid (U. R. Nayak S. Dev, Tetrahedron 8, 42–48 (1960)) or with boron trifluoride etherate (R. E. Beyler, G. Ourisson, J. Org. Chem., 30, 2838–2839 (1965)) to give isolongifolene (2). Subsequent controlled
- (a) oxidation of isolongifolene (2) with sodium bichromate in glacial acetic acid (DE 1804711) or
- (b) air oxidation of isolongifolene (2) (Organikum 16, 169-170 (1986)) (G. Färber "Riechstoffe aus Isolongifolen" (Fragrances from Isolongifolene), Parfümerie+Kosmetik, 68, 18 (1987))

led to isolongifolenone (3).

Isolongifolenone (3) was then reduced in a manner known per se to give a mixture of the epimer alcohols 4a and 4b, the mass ratio of 4a:4b depending on the reaction conditions chosen. The chiral alcohols 4a/b were converted as a mixture or in pure form in a manner known per se into the epimeric methyl ethers 5a and 5b.

The preparation of the epimeric ethyl, propyl, iso-propyl, butyl, sec-butyl, isobutyl and tert-butyl ethers (compounds 6a/b–12a/b) was carried out in an analogous manner (cf. the preparation procedures below).

The stereochemical ratios remain essentially unchanged during the reaction of the isolongifolenol epimer mixture 4a/b or of the pure epimers 4a or 4b to give the novel ethers of the general formula A, meaning that the novel ethers of the general formula A were also present depending on the stereochemical composition of the isolongifolenol as epimer mixtures or pure epimers. With regard to the isolongifolenol epimer mixtures 4a/b, it must also be taken into consideration that the epimeric alcohols 4a and 4b can form in varying amounts depending on the reaction conditions chosen during the reduction of the isolongifolenone (3), meaning that, following etherification, the epimeric methyl ethers 5a and 5b can likewise be present in varying quantitative ratios.

Corresponding to the above statements, starting from (+)-longifolene (1) via the chiral isolongifolenols 4a/b, the corresponding likewise chiral ethers of the general formula A were obtained. (+)-Longifolene (1) is, because of its low-cost availability, currently and must also in the future be the preferred starting compound for the preparation of isolongifolenol derivatives in industrial practice. When this starting compound is used, the stereochemistry of the corresponding isolongifolenyl ethers according to the invention is fixed with the exception of the carbon carrying the ether function. The hydrogen on the bridgehead of the five-membered rings is α-configured.

Starting from the epimeric (−)-longifolene present in Pinus ponderosa, the corresponding isolongifolenyl ethers which are stereochemically different from the compounds 5a/b–12a/b were also synthesized in an analogous manner. These do not differ significantly in their properties from the ethers which were obtained starting from (+)-longifolene (1). In FIG. 1 and the text below, the invention is therefore only illustrated for the sake of clarity with reference to the compounds based on (+)-longifolene (1). For the compounds obtainable starting from (−)-longifolene, the corresponding statement applies in each case.

In a process for the preparation of a cyclic isolongifolenyl ether according to the invention, isolongifolenol is therefore reacted in enantiomerically pure form or as an enantiomer mixture either under acid-catalyzed conditions with an aliphatic alcohol (alkyl hydroxide) or under base-catalyzed conditions with an alkyl halide or alkyl sulfate in an aprotic solvent, the respective alkyl function corresponding to the radical R of the cyclic isolongifolenyl ether of the general formula A.

The novel ethers of the formula A have in each case in pure form or as stereoisomer mixtures original fragrance properties and can advantageously be used in pure form or as isomeric mixtures as fragrances or constituent of perfume oils.

EXAMPLE 1

Preparation of Isolongifolene (2)

Over the course of 60 minutes, 816 g (3.16 mol) of (+)-longifolene (1) (80%, ex turpentine oil, Indian $(\alpha)_D$=+ 39.6°) were added dropwise to a solution, heated to 60° C., of 360 g of toluene and 40 g (0.28 mol) of $BF_3$ etherate, and then the mixture was cooled to room temperature and washed with sodium carbonate solution and water until neutral. After drying over $Na_2SO_4$, the solvent was distilled off under reduced pressure. This gave 800 g (74% according to GC) of crude product.

Gas chromatogram (Shimadzu GC 14A), DB1, 30 m, 100–240° C., 10° C./min $R_t$=5.16 min., 2 (74%)

EXAMPLE 2

Preparation of Isolonqifolenone (3)

A three-necked flask fitted with reflux condenser and dropping funnel was charged with 800 g (2.90 mol) of isolongifolene (2) (74% pure according to GC) from Example 1 and 1 l of ether. Then, over a period of 1.5–2 h at a temperature of 15–20° C., a solution of 1.5 kg of water, 300 g of $H_2SO_4$, 98% strength and 500 g (1.69 mol) of $K_2Cr_2O_7$ was added dropwise, and the mixture was after-stirred and worked up for 20 h at 20° C. The separated-off organic phase was washed with sodium carbonate solution and water until neutral and dried over $Na_2SO_4$, and the solvent was distilled off under reduced pressure. This gave 680 g of crude product.

GC (Conditions see Example 1)

3 $R_t$=12.2 min (48%)

Distillation over a 40 cm metal packed column gave 286 g b.p.$_{.5\ mm}$ 105–108° C., m.p. 39–40°

GC (Condition see Example 1): 3 (96.8%).

GC/MS: HP 5985 A DBWAX, 60 N, 60 m, 60–240° C., 4° C./min.

3 $R_t$=40.7 min.

MS (70 eV): m/z (%)=218 (60 M$^+$), 203 (15), 189 (10), 175 (100), 162 (73), 147 (72), 133 (30), 119 (33), 91 (36), 41 (25). $^{13}$C-NMR (CDCl$_3$), (Varian VXR 300): δ (ppm): 24.56, 25.38, 25.76, 26.98 (CH3), 24.32, 27.83, 36.68, 49.88 (CH2), 46.49, 116.81 (CH), 34.41, 44.00, 58.59, 183.78, 199.98 (C)

EXAMPLE 3

Preparation of a Mixture of Isolongifolenol 4a/4b (2:3)

A three-necked flask fitted with reflux condenser, dropping funnel and thermometer was charged with 100 g (0.44 mol) of isolongifolenone (3) (96.8% according to GC) from Example 2 and 100 g of methanol. Then, over a period of 1 h at 40–50° C., a solution of 150 g of water, 1 g of NaOH and 5 g (0.13 mol) of NaBH$_4$ was added dropwise, the mixture was after-stirred for 6 h at 40–50° C., cooled to room temperature and worked up. 200 g of water and 100 g of ether were added, the organic phase was separated off, the waters were extracted with 100 g of ether, and the combined organic phases were washed until neutral and dried over $Na_2SO_4$. The solvent was then distilled off under reduced pressure. This gave 98 g of crude product.

GC (Conditions see Example 1): 4a (30.9%), 4b (59.8%)

Subsequent fine distillation over a 15 cm Vigreux column gave 88 g b.p.$_{.2\ mm}$ 110–112° C.

GC (Conditions see Example 1): 4a (32.4%), 4b (65.3%)

GC/MS: Conditions see Example 2

4a $R_t$=38.86 min. MS (70 eV): m/z (%)=220 (11, $M^+$), 205 (11), 191 (3), 177 (18), 159 (9), 137 (100), 121 (30), 107 (15), 91 (18), 41 (22).

4b $R_t$=40.14 min. MS (70 eV): m/z (%)=220 (13, $M^+$), 205 (12), 191 (3), 177 (19), 159 (9), 137 (100), 121 (29), 107 (16), 91 (18), 43 (23)

EXAMPLE 4

Isolation of Isolongifolenol 4b

By recrystallizing 10 g of the isolongifolenole 4a (32.4%), 4b (65.3%) obtained from Example 3, from 10 g of a 63/80 hexane fraction, 5.8 g of isolongifolenol (4b) were obtained as colorless crystals (, m.p. 89–90° C.).

GC (Conditions see Example 1): 4b (98.1%)

GC/MS (Conditions see Example 2)

4b $R_t$=40.16 min. MS (70 eV): m/z (%): 220 (14, $M^+$), 205 (13), 191 (4), 177 (23), 159 (11), 137 (100), 121 (31), 107 (17), 91 (19), 43 (23). $^{13}$C-NMR (CDCl$_3$), (Varian VXR 300): δ (ppm): 24.84, 25.29, 26.64, 28.84 ($\underline{C}$H3), 24.72, 28.90, 36.56, 44.26 ($\underline{C}$H2), 46.81, 67.61, 11.46 ($\underline{C}$H), 33.24, 41.94, 56.54, 159.32($\underline{C}$).

EXAMPLE 5

Preparation of a Mixture of Isolongifolenol 4a/4b (1:10)

A three-necked flask fitted with dropping funnel, Vigreux column with attached column head and thermometer was charged with 200 ml of 1 molar aluminum isopropylate solution, which was heated to boiling. Then, over the course of 3 h, a solution consisting of 44 g (0.195 mol) of isolongifolenone (3) (96.8% pure from Example 2) dissolved in 200 ml of isopropanol was added dropwise. At the same time, 150 ml of solvent mixture were distilled off during the dropwise addition at the column head. The mixture was then cooled to room temperature, 200 g of water and 100 g of ether were added, the organic phase was separated off, the waters were extracted again with 100 g of ether and the combined organic phases were neutralized with 1×100 g of 10% strength HCl and then with sodium carbonate solution and water. The mixture was then dried over $Na_2SO_4$ and the solvent was distilled off under reduced pressure. This gave 42 g of crude product.

GC (Conditions see Example 1): 4a (8.9%), 4b (82.3%)

EXAMPLE 6

Preparation of a Mixture of Isolongifolenole 4a/4b (95:5)

A three-necked flask fitted with reflux condenser, thermometer and dropping funnel was charged with 10 g (0.044 mol) of isolongifolenone (3) (96.8% according to GC) from Example 2 and 50 ml of anhydrous THF with nitrogen feed, the mixture was cooled to 0–5° C. and, at this temperature, 50 ml (0.05 mol) of lithium tri-sec-butylborohydride (L-Selectride, Aldrich) were added. The mixture was then after-stirred for 4 h at 0–5° C., poured out onto ice and worked up. The organic phase was separated off, the waters were extracted with 50 ml of ether, the combined organic phases were dried over $Na_2SO_4$ and the solvent was distilled off under reduced pressure. This gave 9.8 g of crude product.

GC (Conditions see Example 1): 4a (86.8%), 4b (4.2%)

EXAMPLE 7

Isolation of Isolongifolenol 4a 2 g of the crude isolongifolenol (4a/4b) obtained from Example 6 were purified by preparative chromatography.

Chromatography conditions: 200 g of silica gel 60, particle size 0.04–0.063 (Merck, Art. No. 9385)

Eluent naphtha/ethyl acetate 9:1,

Initial weight 2 g

Yield: 1.21 g

GC (Conditions see Example 1): 4a (99.1%)

GC/MS (Conditions see Example 2)

4a $R_t$=38.86 min. MS (70 eV): m/z (%)=220 (11, $M^+$), 205 (11), 191 (3), 177 (18), 159 (9), 137 (100), 121 (30), 107 (15), 91 (18), 41 (22). $^{13}$C-NMR (CDCl$_3$), (Varian VXR-300): δ (ppm): 25.51, 26.60, 26.90, 28.23 ($\underline{C}$H3), 24.64, 28.29, 36.97, 43.17 ($\underline{C}$H2), 46.49, 65.97, 113.21 ($\underline{C}$H), 30.68, 42.32, 56.75, 159.76 ($\underline{C}$).

EXAMPLE 8

Preparation of a Mixture of Isolongifolenyl Methyl Ether 5a/5b (2:3)

A three-necked flask fitted with dropping funnel, thermometer and reflux condenser was charged with 20 g (0.089 mol) of isolongifolenol (4a/b) (97.7% according to GC) from Example 3 and 100 ml of methyl tert-butyl ether. 4 g (0.1 mol) of NaH 60% strength (in paraffin) were then added in portions, and the mixture was heated to boiling and stirred under reflux for 2 h. The mixture was then cooled to 70–80° C. and 14.2 g (0.1 mol) of methyl iodide were added dropwise over a period of 30 min. The mixture was stirred under reflux for a total of 6 h, cooled to room temperature and poured out onto water, and the organic phase was separated off. The waters were extracted with 50 ml of ether, and the combined organic phases were washed with water until neutral, dried over $Na_2SO_4$ and the solvent was distilled off under reduced pressure. This gave 21.4 g of crude product.

GC (Conditions see Example 1): 5a (20.8%), 5b (53.4%)

Subsequent fine distillation on a spinning band column gave 11.8 g b.p.$_{.2\ mm}$ 139–140° C.

D 20/4=0.9710 n 20/D=1.4983

GC (Conditions see Example 1): 5a (37.6%), 5b (59.1%)

GC/MS: Conditions see Example 2

5a $R_t$=28.59 min. MS (70 eV): m/z (%): 234 (18, $M^+$), 219 (20), 191 (10), 159 (11), 151 (100), 135 (21), 119 (10), 105 (11), 91 (13), 41 (10).

5b $R_t$=29.09 min. MS (70 eV): m/z (%): 234 (20, $M^+$), 219 (18), 191 (9), 159 (10), 151 (100), 135 (23), 119 (10), 105 (12), 91 (14), 41 (10).

EXAMPLE 9

Isolation of Isolongifolenyl Methyl Ether 5b 2 g of the distillate 5a (37.6%), 5b (59.1 %) obtained from Example 8 were purified by preparative chromatography.

Chromatography conditions: 300 g silica gel 60, particle size 0.04–0.063 (Merck, Art. No. 9385)

Eluent: naphtha/ethyl acetate=98/2

Initial weight: 2 g

Yield: 651 mg

GC (Conditions see Example 1): 5b (97.8%)

GC/MS: Conditions see Example 2

5b $R_t$=29.09 min. MS (70 eV): m/z (%): 234 (21, M$^+$), 219 (19), 191 (9), 159 (11), 151 (100), 135 (23), 119 (10), 105 (12), 91 (19), 41 (10) $^{13}$C-NMR (CDCl$_3$), (Varian VRX-300): δ (ppm): 24.96, 25.27, 26.77, 28.85, 55.38 (CH$_3$), 24.70, 28.74, 36.57, 39.86 (CH$_2$), 46.83, 76.17, 111.82 (CH), 32.92, 42.01, 56.60, 159.39(C).

EXAMPLE 10

Preparation of a Mixture of Isolongifolenyl Methyl Ether 5a/5b (9:1)

A three-necked flask fitted with reflux condenser, thermometer and dropping funnel was charged with 7 g (0.029 mol) of isolongifolenol (4a/b) (91% strength according to GC) from Example 6 and 50 ml of toluene (anhydrous), 1.2 g (0.03 mol) of sodium hydride, 60% strength (in paraffin) were added in portions over a period of 30 min, and the mixture was heated to boiling and stirred under reflux for 1 h. Then, over the course of 30 min, 30.8 g (0.03 mol) of dimethyl sulfate were added dropwise, and the mixture was stirred for a further 5 h under reflux and cooled to room temperature, and 50 g of water and 30 ml of ether were added, the organic phases were separated off, the waters were extracted with 30 ml of ether, the organic phases were washed with water until neutral, dried over Na$_2$SO$_4$ and the solvent was distilled off under reduced pressure. This gave 6.8 g of crude product.

GC (Conditions see Example 1): 5a (78.1%), 5b (6.9%)

EXAMPLE 11

Isolation of Isolongifolenyl Methyl Ether 5a 5 g of the crude mixture obtained from Example 10 were distilled on a Fischer Spaltrohr column.

Yield: 2.5 g.

D 20/4=0.9701 n 20/D=1.4978

GC (Conditions see Example 1): 5a (98.4%)

GC/MS (Conditions see Example 2)

5a $R_t$=28.59 min. MS (70 eV), m/z (%): 234 (19, M$^+$), 219 (20), 191 (10), 159 (11), 151 (100), 135 (21), 119 (10), 105 (12), 91 (14), 41 (12). $^{13}$C-NMR (CDCl$_3$), (Varian VXR-300): δ (ppm): 25.57, 26.26, 26.69, 28.41, 56.17 (CH$_3$), 24.71, 28.23, 36.97, 38.28 (CH$_2$), 46.56, 74.84, 110.91 (CH), 30.67, 42.26, 56.89, 159.99(C).

EXAMPLE 12

Preparation of a Mixture of Isolongifolenyl Ethyl Ether 6a/b

A three-necked flask fitted with dropping funnel, thermometer and reflux condenser was charged with 15 g (0.067 mol) of isolongifolenol (4a/b) (97.7% according to GC) from Example 3 and 50 ml of toluene. 3.2 g (0.08 mol) of NaH 60% strength (in paraffin) were then added in portions under a nitrogen atmosphere over a period of 45 min, and the mixture was heated to boiling and stirred under reflux for 1 h. 10.4 g (0.08 mol) of diethyl sulfate were then added dropwise over the course of 1 h, the mixture was stirred under reflux for a further 8 h and cooled to room temperature, water was added and the organic phase was separated off. The waters were extracted once with 50 ml of ether, and the combined organic phases were washed with water, dried over Na$_2$SO$_4$ and the solvent was distilled off under reduced pressure. This gave 16.3 g of crude product.

GC (Conditions see Example 1): 6a (24.6%), 6b (53.4%)

Subsequent fine distillation on a spinning belt column gave 6.8 g b.p.$_{2\ mm}$ 141–143° C.

D 20/4=0.9730 n 20/D=1.4986

GC (Conditions see Example 1): 6a (30.1%), 6b (68.1%)

GC/MS: Conditions see Example 2

6a $R_t$=27.66 min. MS (70 eV), m/z (%), 248(28, M$^+$), 233(26), 205(10),165(100), 149(22), 137 (22), 119 (14), 105 (16), 91 (19), 41 (18).

6b $R_t$=29.35 min. MS (70 eV), m/z (%), 248 (29, M+), 233 (27), 205 (10), 165 (100), 149 (22), 137 (23), 119 (15), 105 (17), 91 (20), 41 (19).

EXAMPLE 13

Preparation of a Mixture of Isolongifolenyl Propyl Ether 7a/7b

A three-necked flask fitted with dropping funnel, thermometer and reflux condenser was charged with 15 g (0.067 mol) of isolongifolenol (4a/b) (97.70% according to GC) from Example 3 and 50 ml of toluene, and at room temperature under a nitrogen atmosphere 3.2 g (0.08 mol) of sodium hydride 60% strength (in paraffin) were added over a period of 45 min, the mixture was heated to boiling and stirred under reflux for 1 h. The mixture was then cooled to 70° C., 7.90 g (0.08 mol) of 1-bromopropane were added dropwise over a period of 15 min, the mixture was stirred under reflux for 4 h and poured out onto water, and the organic phase was separated off and the waters were extracted with 50 ml of ether. The combined organic phases were washed once with water and dried over Na$_2$SO$_4$, and the solvent was distilled off under reduced pressure. This gave 14.8 g of crude product.

GC (Conditions see Example 1): 7a (20.4%), 7b (50.3%)

Subsequent fine distillation on a spinning band column gave 4.3 g b.p.$_{2\ mm}$ 144–146° C.

GC (Conditions see Example 1): 7a (29.4%), 7b (69.1%)

GC/MS (Conditions see Example 2)

7a $R_t$=30.26 min. MS (70 eV), m/z (%), 262 (52, M$^+$), 247 (37), 179 (100),163 (23),147 (21), 137 (60), 121 (20), 119 (21), 105 (20), 91 (19), 41 (24).

7b $R_t$=31.72 min. MS (70 eV), m/z (%), 262 (41, M$^+$), 247 (31), 179 (100), 163 (23), 137 (65), 121 (22), 119 (19), 105 (21), 91 (25), 41 (36).

EXAMPLE 14

Preparation of a Mixture of Isolongifolenyl Isopropyl Ether 8a/b

The reaction was carried out analogously to the procedure given in Example 12, with the addition of 2-bromopropane.

GC/MS: Conditions see Example 2

8a $R_t$=27.93 min.

MS (70 eV), m/z (%), 262 (32, M$^+$), 220 (19), 205 (23), 177 (23), 163 (27), 137 (100), 121 (26), 107 (16), 91 (16), 41 (17).

8b $R_t$=29.11 min. MS (70 eV), m/z (%), 262 (32, M$^+$), 220 (18), 205 (22), 177 (22), 163 (27), 137 (100), 121 (26), 107 (16), 91 (15), 41 (17).

EXAMPLE 15

Preparation of a Mixture of Isolongifolenyl n-butyl Ether 9a/b

The reaction was carried out analogously to the procedure given in Example 12, with the addition of 1-bromobutane.

GC/MS: Conditions see Example 2

9a $R_t$=32.19 min. MS (70 eV), m/z (%), 276 (45, M$^+$), 261 (39), 203 (25), 193 (100), 177 (24), 137 (84), 121 (27), 105 (22), 91 (20), 41 (28).

9b $R_t$=32.61 min. MS (70 eV), m/z (%), 276 (46, M$^+$), 261 (39), 203 (25), 193 (100), 177 (24), 137 (84), 121 (27), 105 (22), 91 (22), 41 (28).

EXAMPLE 16

Preparation of a Mixture of Isolongifolenyl Sec-butyl Ether 10a/b

The reaction was carried out analogously to the procedure given in Example 12, with the addition of 2-bromobutane.

GC/MS: Conditions see Example 2

10a $R_t$=30.17 min. MS (70 eV), m/z (%), 276 (15, M$^+$), 220 (21), 205 (17), 177 (24), 163 (21), 137 (100), 121 (21), 105 (13), 91 (14), 41 (15).

10b $R_t$=30.55 min. MS (70 eV), m/z (%), 276 (15, M$^+$), 220 (22), 205 (17), 177 (24), 163 (21), 137 (100), 121 (20), 105 (13), 91 (13), 41 (15).

EXAMPLE 17

Preparation of a Mixture of Isolongifolenyl Isobutyl Ether 11 a/b

The reaction was carded out analogously to the procedure given in Example 12, with the addition of 2-bromo-2-methylpropane.

GC/MS: Conditions see Example 2

11a $R_t$=27.96 min. MS (70 eV), m/z (%), 276 (6, M$^+$), 220 (66), 203 (13), 177 (33), 163 (73), 137 (100), 121 (34), 105 (18), 91 (20), 41 (22).

11b $R_t$=29.27 min. MS (70 eV), m/z (%), 276 (10, M$^+$), 220 (72), 205 (16), 177 (40), 163 (80), 137 (100), 121 (39), 107 (18), 91 (16), 41 (16).

EXAMPLE 18

Preparation of a Mixture of Isolongifolenyl Tert-butyl Ether 12a/b

The reaction was carried out analogously to the procedure given in Example 12, with the addition of tert-butyl bromide.

GC/MS: Conditions see Example 2

12a $R_t$=30.19 min. MS (70 eV), m/z (%), 276 (24, M$^+$), 221 (60), 193 (67), 177 (50), 161 (49), 137 (100), 121 (50), 105 (51), 91 (57), 41 (34).

12b $R_t$=31.38 min. MS (70 eV), m/z (%), 276 (16, M$^+$), 221 (27), 205 (34), 193 (48), 177 (18), 137 (100), 121 (30), 105 (21), 91 (22), 41 (28).

EXAMPLE 19

Odor Description of Ethers 5a/b to 12a/b

The odor assessment was carried out by a panel of experts using smelling strips.

5a/b from Example 8:
strongly musk, powdery, Cashmeran, ambergris, exalting, weakly woody 5a from Example 11:
musk, slightly floral, Cashmeran, exalting, spicy 5b from Example 9:
ambergris, dry musk, slightly spicy, weakly woody-Patchouli 6a/b from Example 12:
dry, slightly powdery-fruity, damp sand, Patchouli 7a/b from Example 13:
powdery musk, floral, slightly earthy 8 a/b from Example 14:
acidic, powdery musk, dry, weakly Patchouli-woody 9 a/b from Example 15:
herby, acidic, weakly green-dusty 10 a/b from Example 16:
herby, slightly acidic, dusty, dry, weakly musk 11 a/b from Example 17:
weakly acidic-herby, dry, earthy 12 a/b from Example 18:
weakly powdery-spicy, slightly metallic-green

EXAMPLE 20

Application Example 1

Perfume Base of the Floral-woody Type

|  | Parts by weight |
|---|---|
| Bergamot oil | 7.5 |
| Linalool | 4.0 |
| Phenylethyl alcohol | 4.0 |
| Benzyl acetate | 1.0 |
| Citronellol | 3.0 |
| Hedion ® (a) | 10.0 |
| Lyral ® (b) | 4.0 |
| Hydroxycitronellal | 3.0 |
| Rose oxide L (c) | 2.5 |
| Hexylcinnamaldehyde, alpha | 7.5 |
| Ysamber-K ® (c) | 3.0 |
| Vetiveryl acetate | 2.0 |
| Brahmanol-F (c) | 2.0 |
| Benzyl salicylate | 2.0 |
| Hexenyl salicylate, cis-3 | 1.0 |
| Cedramber (b) | 1.0 |
| Cindol 80 (c) | 0.5 |
| Opoponax extract | 0.5 |
| Oak moss extract 50% strength in DPG | 7.0 |
|  | 65.5 |

(a) Firmenich
(b) IFF
(c) DRAGOCO

Because of the presence of Ysamber K (a cyclic isolongifolenyl ketal, as disclosed in the already mentioned EP-A 0 543 470), in particular, the perfume base of the given formula has a balanced floral-woody scent character, the radiance of which becomes clear in the top note by the addition of 10 parts of 5a/b (from Example 8) and is intensified with strong emphasis of the floral note. In the residual odor, the soft, powdery silky odor impressions are more strongly emphasized, with a marked accent in the direction of a natural musk scent. In this connection, as well as a significant harmonization, increased adhesion of the residual odor is also to be established in particular.

EXAMPLE 21

| Perfume base of the Fougère type | |
|---|---|
| | Parts by weight |
| Bergamot oil | 18.0 |
| Lavandin oil, super | 15.0 |
| Lilial ® (b) | 10.0 |
| Anisaldehyde | 3.0 |
| Coumarin | 5.0 |
| Hexylcinnamaldehyde, alpha | 20.0 |
| Ambrinol expoxide, alpha (c) | 0.5 |
| Ambrocenide 10 ® (c) | 0.1 |
| Cantryl (c) | 5.0 |
| Peppermint oil | 1.0 |
| | 77.6 |

(b) IFF
(c) DRAGOCO

The perfume base of the given formula has a fresh-herby Fougere scent. The addition of 10 parts of 5a/b (from Example 8) intensifies in particular the top note, the perfume base gaining significantly in intensity in the floral direction. The herby aspects decrease in intensity and appear overall more rounded off and clearly harmonized. A significant accent in the direction of a natural musk scent is to be established particularly in the residual odor.

The alternative addition of 10 parts of 6a/b effects, in addition to an overall rounded off base, a significant emphasizing of long-lasting animalic-earthy aspects (Patchouli), the dry-exalting odor impressions in particular experiencing intensification.

What is claimed is:

1. A method for modifying the fragrance of a cometic composition, a laundry detergent composition, a household cleaning composition or a personal hygiene composition, the method comprising adding to said composition a fragrance mixture or perfume oil comprising as a fragrance or constituent a cyclic isolongifolenyl ether of the general formula A:

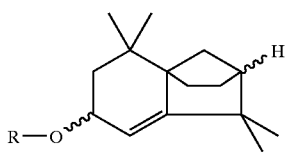

where wavy lines mean α- as well as β-configuration, and R is the following radicals:

R=Me, Et, Pr, iso-Pr, Bu, sec-Bu, iso-Bu, tert-Bu.

2. A method for strengthening the top note of a perfume composition, the method comprising adding to said perfume composition a top note strengthening effective amount of a cyclic isolongifolenyl ether of the general formula A:

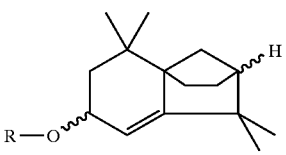

where wavy lines mean α- as well as β-configuration, and R is the following radicals:

R=Me, Et, Pr, iso-Pr, Bu, sec-Bu, iso-Bu, tert-Bu.

3. A method for rounding off and/or harmonizing the main notes of a fragrance composition, the method comprising adding to said fragrance composition an effective amount of a cyclic isolongifolenyl ether of the general formula A:

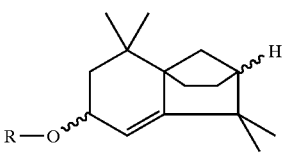

where wavy lines mean α- as well as β-configuration, and R is the following radicals:

R=Me, Et, Pr, iso-Pr, Bu, sec-Bu, iso-Eu, tert-Bu.

4. A method for conveying or strengthening a musk and/or patchouli aspect in a fragrance composition, the method comprising adding to said fragrance composition an effective amount of a cyclic isolongifolenyl ether of the general formula A:

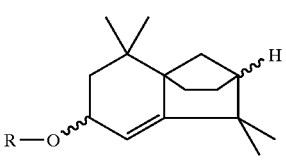

where wavy lines mean α- as well as β-configuration, and R is the following radicals:

R=Me, Et, Pr or iso-Pr.

5. A method as in claim 4, wherein R=methyl.

6. A fragrance composition or perfume base comprising as a fragrance or fragrance constituent a cyclic isolongifolenyl ether of the general formula A:

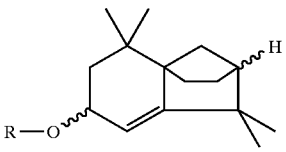

where wavy lines mean α- as well as β-configuration, and R is the following radicals:

R=Me, Et, Pr, iso-Pr, Bu, sec-Bu, iso-Bu, tert-Bu.

7. A fragrance composition or perfume base as in claim 6, wherein said cyclic isolongifolenyl ether of the general formula A is present in a top note strengthening effective amount.

8. A fragrance composition or perfume base as in claim 6, wherein said cyclic isolongifolenyl ether of the general formula A is present in an amount effective for rounding off and/or harmonizing the main notes of a fragrance composition.

9. A fragrance composition or perfume base as in claim 6, wherein R=Me, Et, Pr or iso-Pr.

10. A fragrance composition as in claim 9, wherein said cyclic isolongifolenyl ether of the general formula A is present in an amount effective for conveying or strengthening a musk aspect.

11. A method as in claim 10, wherein R=methyl.

12. A fragrance composition as in claim 9, wherein said cyclic isolongifolenyl ether of the general formula A is present in an amount effective for conveying or strengthening a patchouli aspect.

13. A method as in claim 12, wherein R=methyl.

* * * * *